(12) United States Patent
Kameyama et al.

(10) Patent No.: US 11,273,169 B2
(45) Date of Patent: Mar. 15, 2022

(54) FOOD FOR IMPROVING INTESTINAL ENVIRONMENT

(71) Applicant: AJINOMOTO CO., INC., Tokyo (JP)

(72) Inventors: Keishi Kameyama, Kanagawa (JP); Momoka Tsuneyoshi, Kanagawa (JP)

(73) Assignee: AJINOMOTO CO., INC., Tokyo (JP)

(*) Notice: Subject to any disclaimer, the term of this patent is extended or adjusted under 35 U.S.C. 154(b) by 0 days.

(21) Appl. No.: 16/821,613

(22) Filed: Mar. 17, 2020

(65) Prior Publication Data

US 2020/0237790 A1 Jul. 30, 2020

Related U.S. Application Data

(63) Continuation of application No. PCT/JP2018/037395, filed on Oct. 5, 2018.

(30) Foreign Application Priority Data

Oct. 5, 2017 (JP) .............................. JP2017-195311

(51) Int. Cl.
*A61K 31/702* (2006.01)
*A23L 33/21* (2016.01)
*A61P 1/00* (2006.01)
*A61K 9/00* (2006.01)
*A61K 38/16* (2006.01)

(52) U.S. Cl.
CPC ............ *A61K 31/702* (2013.01); *A23L 33/21* (2016.08); *A61K 9/0095* (2013.01); *A61K 38/16* (2013.01); *A61P 1/00* (2018.01); *A23V 2002/00* (2013.01)

(58) Field of Classification Search
None
See application file for complete search history.

(56) References Cited

U.S. PATENT DOCUMENTS

| | | | |
|---|---|---|---|
| 2005/0019388 A1* | 1/2005 | Furuta | A61K 9/4816 424/452 |
| 2007/0207187 A1 | 9/2007 | Yajima et al. | |
| 2008/0075831 A1 | 3/2008 | Hirano et al. | |

FOREIGN PATENT DOCUMENTS

| | | | | |
|---|---|---|---|---|
| CN | 1296784 A | * | 5/2001 | ............ A23L 2/38 |
| CN | 103283834 A | * | 9/2013 | ............ A23C 9/13 |
| CN | 108064944 A | | 5/2018 | |
| JP | 62-074259 A | | 4/1987 | |
| JP | 05-137533 A | | 6/1993 | |
| JP | 2003-235492 A | | 8/2003 | |
| JP | 2005-185270 A | | 7/2005 | |
| JP | 2006-149371 A | | 6/2006 | |
| JP | 2006-262895 A | | 10/2006 | |
| JP | 2007-022982 A | | 2/2007 | |
| JP | 2011-178764 A | | 9/2011 | |

OTHER PUBLICATIONS

Tanimoto, H., Mori, M., Motoki, M., Torii, K., Kadowaki, M., & Noguchi, T. (2001). Natto mucilage containing poly-γ-glutamic acid increases soluble calcium in the rat small intestine. Bioscience, biotechnology, and biochemistry, 65(3), 516-521. (Year: 2001).*
International Search Report for PCT Patent App. No PCT/JP2018/037395 (dated Jan. 8, 2019) with English translation thereof.
Kameyama, K., "The effects of γ-PGA on growth stimulation of gut bifidobacteria and inhibition of intestinal permeability" Med. Sci. Digest 2016;42(6):295-298, with partial English translation.
Jin, H.-E., et al., "Prebiotic Effects of Poly-Gamma-Glutamate on Bacterial Flora in Murine Gut," J. Microbiol. Biotechnol. 2017;27(2):412-415.
"Sugar assimilability by intestinal bacteria," Meiji Food Materia Co., Ltd., "Meioligo (registered trade name)" pamphlet, [online], Jul. 2017, [retrieval date Dec. 12, 2018], internet:<URL:https://www.meijifm.co.jp/products/material/oligo/meioligo/pdf/comparison.pdf>, 2. pp, with partial English language translation.
Tanaka, A., "Fat substitution dietary fiber inulin," J. Cookery Sci. Japan 2013;46(4):312-313, with partial English language translation.
Extended European Search Report from European Patent App. No. 18864664.0 (dated Jun. 7, 2021).

* cited by examiner

*Primary Examiner* — Dale R Miller
(74) *Attorney, Agent, or Firm* — Cermak Nakajima & McGowan LLP; Shelly Guest Cermak

(57) ABSTRACT

The present invention provides a food that is effective for improving the intestinal environment by promoting proliferation of intestinal lactic acid bacteria and the like. The present invention provides a food that is effective for improving the intestinal environment, wherein the food includes (1) γ-polyglutamic acid or a composition containing γ-polyglutamic acid, and (2) oligosaccharide or a composition containing oligosaccharide.

14 Claims, 4 Drawing Sheets

Specification includes a Sequence Listing.

SEQUENCE LISTING

```
<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
agcagtaggg aatcttcca                                              19
```

```
<210> SEQ ID NO 2
<211> LENGTH: 17
<212> TYPE: DNA
<213> ORGANISM: Artificial Sequence
<220> FEATURE:
<223> OTHER INFORMATION: primer

<400> SEQUENCE: 2
caccgctaca catggag                                                  17

<210> SEQ ID NO 3
<211> LENGTH: 17
<212> TYPE: DNA
<213> ORGANISM: Artificial Sequence
<220> FEATURE:
<223> OTHER INFORMATION: primer

<400> SEQUENCE: 3
ctcctggaaa cgggtgg                                                  17

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
ggtgttcttc ccgatatcta ca                                            22
```

FOOD FOR IMPROVING INTESTINAL ENVIRONMENT

This application is a continuation of, and claims priority under 35 U.S.C. § 120 to, International Application No. PCT/JP2018/037395, filed Oct. 5, 2018, and claims priority therethrough under 35 U.S.C. § 119 to Japanese Patent Application No. 2017-195311, filed Oct. 5, 2017, the entireties of which are incorporated by reference herein. Also, the Sequence Listing filed electronically herewith is hereby incorporated by reference (File name: 2020-03-17T_US-608_Seq_List; File size: 1 KB; Date recorded: Mar. 17, 2020).

BACKGROUND

Technical Field

The present invention relates to a food for improving the intestinal environment by promoting proliferation of intestinal lactic acid bacteria and bifidobacteria.

Background Art

It is important for the prevention of various diseases and the promotion and maintenance of good health to promote proliferation of beneficial bacteria, such as intestinal lactic acid bacteria, bifidobacteria, and the like; and to improve the intestinal environment by the normalization of intestinal bacterial flora.

JP-A-2007-22982 describes the improvement of bowel movements by γ-polyglutamic acid. The reference J. Microbiol. Biotechnol. ((2017), 27(2), 412-415) describes an increase in lactic acid bacteria by γ-polyglutamic acid. It is known that oligosaccharides are difficult to digest and be absorbed in the stomach and small intestine, and that they reach the large intestine and become bait for beneficial bacteria such as lactic acid bacteria, bifidobacteria, and the like. However, it is not known whether the combined use of γ-polyglutamic acid and oligosaccharide can appreciably increase lactic acid bacteria and bifidobacteria as compared to when each are used alone.

SUMMARY

The present invention provides a food for improving the intestinal environment by promoting proliferation of intestinal lactic acid bacteria and bifidobacteria.

It has been found that the combined use of γ-polyglutamic acid and oligosaccharide remarkably increases lactic acid bacteria and bifidobacteria as compared to when each are used alone.

It is an aspect of the present invention to provide a food for improving intestinal environment, the food comprising (1) γ-polyglutamic acid or a composition comprising γ-polyglutamic acid, and (2) oligosaccharide or a composition comprising oligosaccharide.

It is a further aspect of the present invention to provide the food as described above, wherein the composition comprising oligosaccharide is in a liquid form.

It is a further aspect of the present invention to provide the food as described above, wherein the composition comprising oligosaccharide in a liquid form is a liquid.

It is a further aspect of the present invention to provide the food as described above, wherein the composition comprising oligosaccharide in a liquid form is a drink.

A food having a remarkably superior effect for promoting proliferation of lactic acid bacteria and bifidobacteria as compared to when each is used singly is described. Also described is a method to improve the intestinal environment by supplying a combination of γ-polyglutamic acid and oligosaccharide.

DETAILED DESCRIPTION

Figure 1:
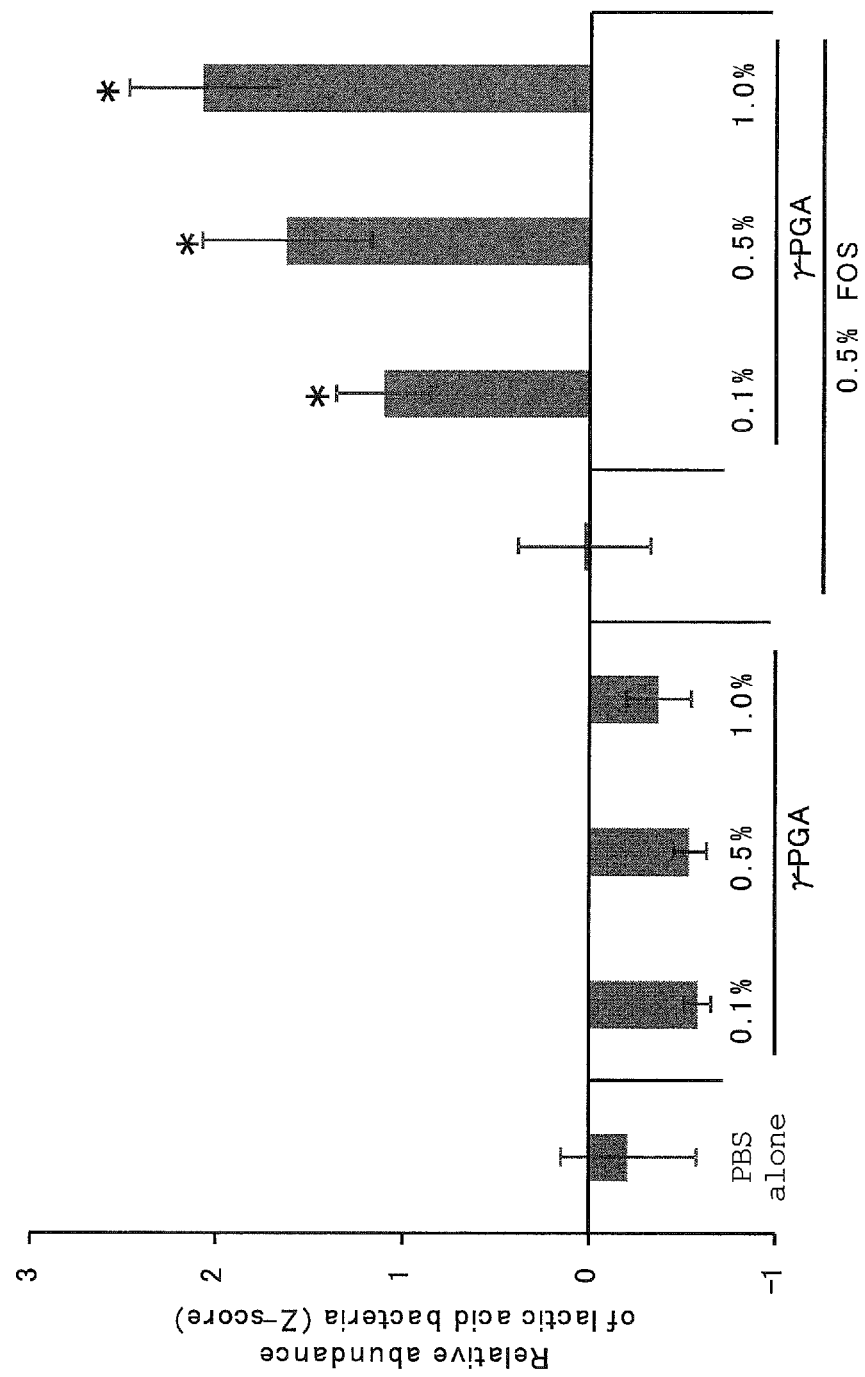
FIG. 1 shows the results (mean±standard error, n=6) of Experimental Example 1, which shows a test of the addition of γ-polyglutamic acid and fructo-oligosaccharide to a human feces suspension.

The food as described herein for improving intestinal environment as described herein is composed of a combination of (1) γ-polyglutamic acid or a composition containing γ-polyglutamic acid, and (2) oligosaccharide or a composition containing oligosaccharide.

The food as described herein is a combined-use food of (1) and (2) in which (1) and (2) are used in combination.

In the food as described herein, (1) and (2) may be simultaneously formulated and be present in the same preparation (food), or the compositions of (1) and (2) may be formulated separately and ingested simultaneously or at different times by the same route or different routes. That is, the food as described herein includes a food containing the compositions of (1) and (2) in one preparation, and a food combining the compositions of (1) and (2), but formulated separately.

As described herein, the term "food" is intended to mean a concept that broadly encompasses foods that can be ingested orally, excluding pharmaceuticals, and can include not only so-called solid "food," but also can include drinks, health supplements, food with health claims, that is, food for specified health uses or foods with functional claims, supplements, and the like.

As used herein, the phrase "improvement of intestinal environment" can refer to a relative increase of lactic acid bacteria and/or bifidobacteria that is present in the lower gastrointestinal tract. A relative increase can mean that lactic acid bacteria and/or bifidobacteria are predominant in the intestinal bacterial flora. The predominance of lactic acid bacteria and bifidobacteria in the intestinal bacterial flora can be confirmed by measuring the amount of lactic acid bacteria and the amount of bifidobacteria in feces by quantitative PCR or the like.

As used herein, the term "lower gastrointestinal tract" can mean the ileum, cecum, colon, and rectum.

(1) γ-Polyglutamic Acid or a Composition Containing γ-Polyglutamic Acid

γ-polyglutamic acid can be used alone, or as a component in a composition as in (1).

γ-polyglutamic acid can be, for example, γ-polyglutamic acid, which is a polymer in which about 30 to about 5000 D-glutamic acids and L-glutamic acids are mixed and bonded in a ratio of about 8:2.

The γ-polyglutamic acid can also be referred to as polyglutamic acid.

As γ-polyglutamic acid, a commercially available product (e.g., CALTAKE (trade name) manufactured by Ajinomoto Co., Inc.) can also be used.

The form of the composition containing γ-polyglutamic acid as described herein is not particularly limited, and may be, for example, a powder, granule (including fine granules), tablet, hard capsule, soft capsule, liquid (e.g., solution, suspension, milky liquid), drink, jelly, pudding, yogurt, candy, chewing gum, or the like. These can be produced by a known method. For example, γ-polyglutamic acid can be mixed with a carrier, such as for example an excipient, binder, disintegrant, lubricant, solvent, and a powder, granule, tablet, capsule, liquid, and the like can be produced by a method known in the field of food preparation or pharmaceutical preparation. In addition, they can also be produced by adding and mixing γ-polyglutamic acid to and with food and drink, such as for example, water or a soft drink.

(2) Oligosaccharide or a Composition Containing Oligosaccharide

Oligosaccharide can be used alone or as a component in a composition as in (2).

Examples of the oligosaccharide can include coffee bean manno-oligosaccharide, lactosucrose oligosaccharide, galacto-oligosaccharide, fructo-oligosaccharide, soybean oligosaccharide, xylo-oligosaccharide and isomalto-oligosaccharide; and fructo-oligosaccharide, coffee bean manno-oligosaccharide, isomalto-oligosaccharide or galacto-oligosaccharide are particular examples. One or more oligosaccharides can be used in combination.

The form of the composition containing oligosaccharide as described herein is not particularly questioned and may be, for example, a powder, granule (including fine granules), tablet, hard capsule, soft capsule, liquid, such as for example a solution, suspension, milky liquid, liquid seasoning (e.g., liquid sweetener); drink, jelly, pudding, yogurt, candy, chewing gum, or the like. Among these, a liquid form such as a liquid, such as for example a solution, suspension, milky liquid, liquid seasoning (e.g., liquid sweetener), and drinks are particular examples.

These compositions can be produced by a known method. For example, oligosaccharide can be mixed with carriers, such as for example an excipient, binder, disintegrant, lubricant, and solvent; and as a result, a powder, granule, tablet, capsule, liquid, and the like can be produced by a method known in the field of food preparation or pharmaceutical preparation. In addition, they can also be produced by adding and mixing oligosaccharide to and with food and drink, such as for example water or a soft drink. In addition, they can also be produced by adding and mixing a liquid sweetener containing oligosaccharide to and with food and drink, such as for example water or a soft drink.

As mentioned above, the food as described herein includes a food containing the above-mentioned (1) and (2) in one preparation, and a food combining the above-mentioned (1) and (2) formulated separately. As the food combining (1) and (2) formulated separately, for example, a food combining (1) in the form of granule, tablet, hard capsule, or soft capsule containing γ-polyglutamic acid, and (2) in the form of drink containing oligosaccharide can be mentioned.

(1) and (2) may be ingested simultaneously or at different times by the same route or different routes. Specifically, for example, a capsule, such as for example a hard capsule or a soft capsule, containing γ-polyglutamic acid, granule, tablet, and the like may be ingested together with an oligosaccharide-containing drink.

The form of the food containing (1) and (2) in one preparation is not particularly questioned and may be, for example, powder, granule (including fine granules), tablet, hard capsule, soft capsule, liquid, such as for example a solution, suspension, milky liquid, liquid seasoning (e.g., liquid sweetener); drink, jelly, pudding, yogurt, candy, chewing gum or the like. These can be produced by a known method.

The ingestion amount of γ-polyglutamic acid in the food for improving intestinal environment as described herein is generally 0.1-100 g, 0.1-50 g, or 1-20 g, per day for an adult (body weight 60 kg).

The ingestion amount of an oligosaccharide in the food for improving intestinal environment as described herein can be generally 0.1-100 g, 0.1-50 g, or 1-20 g, per day for an adult (body weight 60 kg).

In the food for improving intestinal environment as described herein, the weight ratio of oligosaccharide and γ-polyglutamic acid (oligosaccharide:γ-polyglutamic acid) can be 1:0.05-20, 1:0.1-10, 1:0.1-5, 1:0.1-3, or 1:0.2-2.

The food as described herein can be safely given to human and animals other than human such as for example mammals and birds such as domestic animals, poultry, experiment animals, and the like. The ingestion form for animals other than human may be as an addition to a feed.

In another embodiment as described herein, "a commercial package containing a food containing a combination of (1) γ-polyglutamic acid or a composition containing γ-polyglutamic acid and (2) oligosaccharide or a composition containing oligosaccharide, and written matter describing how to use the food for improving intestinal environment", "a food with an indication that it can be used for improving intestinal environment, which contains a combination of (1) γ-polyglutamic acid or a composition containing γ-polyglutamic acid, and (2) oligosaccharide or a composition containing oligosaccharide", "a food for enhancing an intestinal environment improving effect containing a combination of (1) γ-polyglutamic acid or a composition containing γ-polyglutamic acid and (2) oligosaccharide or a composition containing oligosaccharide" and "a food for enhancing an intestinal environment improving effect of a oligosaccharide or a composition containing oligosaccharide, which food is a γ-polyglutamic acid or a composition containing γ-polyglutamic acid" can be mentioned. The "γ-polyglutamic acid or a composition containing γ-polyglutamic acid", "an oligosaccharide or a composition containing oligosaccharide", "intestinal environment improvement", "ingestion amount of γ-polyglutamic acid" and "ingestion amount of oligosaccharides" are the same as exemplifications and definitions indicated for the above-mentioned food for improving intestinal environment.

EXAMPLES

The present invention is explained in more detail by referring to the following Experimental Examples, Examples, Comparative Examples, and Reference Examples, which are not to be construed as limiting.

Abbreviations mean the following:
γ-PGA: γ-polyglutamic acid (Poly-γ-Glutamic Acid)
FOS: fructo-oligosaccharide
PBS: phosphate buffered saline
CMOS: coffee bean manno-oligosaccharide IMOS: isomalto-oligosaccharide
GOS: galacto-oligosaccharide Experimental Example 1: Addition Test of γ-PGA and Fructo-Oligosaccharide to Human Feces Suspension The PBS solutions of Examples and Comparative Examples shown in Table 1 were prepared and used as media for feces culture. PBS alone was used as a negative control. As γ-PGA, polyglutamic acid "CALTAKE" manufactured by Ajinomoto Co., Inc. was used, and as FOS, fructo-oligosaccharide manufactured by Wako Pure Chemical Industries, Ltd. was used.

Thereafter, 10 ml each was dispensed into glass vials and the glass vials were sterilized by autoclave, made anaerobic, and sealed with a butyl rubber stopper. The feces suspension was prepared by collecting about 10 g of feces from 6 healthy individuals (3 men and 3 women) in their 20s to 40s and suspending same in 80 ml of anaerobic PBS. The feces suspension was added to each vial by 0.5 ml, placed in an incubator at 37° C., and anaerobically cultured for 4 days with tumble blending once per day. After completion of the culture, an intestinal bacterial pellet was obtained from the whole amount of the culture medium by centrifugation (8,000 xg, for 5 min). DNA was extracted from this pellet using ISOFECAL for BeadsBeat (manufactured by NIPPON GENE CO., LTD.), and quantitative PCR was performed using GeneAce SYBR qPCR Mix α (manufactured by NIPPON GENE CO., LTD.). Quantitative PCR was performed under the conditions of 45 cycles of 95° C. for 30 sec and 60° C. for 60 sec after 95° C. for 10 min. Primers for quantitative PCR used for detection of lactic acid bacteria group (mainly, *Lactobacillus* spp.) were as follows.

```
LAB-F:
                                       (SEQ ID NO: 1)
5'-AGCAGTAGGGAATCTTCCA-3'
(Appl Environ Microbiol. 67(6): 2578-2585, 2001)

LAB-R:
                                       (SEQ ID NO: 2)
5'-CACCGCTACACATGGAG-3'
(Appl Environ Microbiol. 68(1): 114-123, 2002)
```

TABLE 1

| | medium for feces culture |
|---|---|
| Example 1-1 | 0.1% γ-PGA and 0.5% FOS-containing PBS solution |
| Example 1-2 | 0.5% γ-PGA and 0.5% FOS-containing PBS solution |
| Example 1-3 | 1.0% γ-PGA and 0.5% FOS-containing PBS solution |
| Comparative Example 1-1 | 0.1% γ-PGA-containing PBS solution |
| Comparative Example 1-2 | 0.5% γ-PGA-containing PBS solution |
| Comparative Example 1-3 | 1.0% γ-PGA-containing PBS solution |
| Comparative Example 2 | 0.5% FOS-containing PBS solution (positive control) |
| Reference Example 1 | PBS alone (negative control) |

Using the results obtained by quantitative PCR, the relative amount when PBS alone (negative control) is 1 was calculated, and the results were normalized with z-score.

The results are shown in FIG. 1. The data shows mean of z-score±standard error (n=6). A significant difference was determined by Dunnet's test using positive control as the control (*: P<0.05).

As a result, proliferation of the lactic acid bacteria group was not observed when γ-PGA was added alone. However, when 0.5% FOS was added together with γ-PGA, more prominent proliferation of the lactic acid bacteria group than that with FOS alone was observed and was concentration dependent.

Thus, a synergistic effect exceeding the additive effect was observed in the proliferation of lactic acid bacteria group by combining γ-PGA and oligosaccharide.

Experimental Example 2: Addition Test of γ-PGA and Various Oligosaccharides to Human Feces Suspension The PBS solutions of Examples and Comparative Examples shown in Table 2 were prepared and used as media for feces culture. PBS alone was used as a negative control. As CMOS, coffee bean manno-oligosaccharide manufactured by Ajinomoto AGF, Inc. was used, as IMOS, isomalto-oligosaccharide manufactured by Wako Pure Chemical Industries, Ltd. was used, and as GOS, galacto-oligosaccharide manufactured by Wako Pure Chemical Industries, Ltd. was used.

Feces culture and detection of lactic acid bacteria were performed according to methods similar to those in Experimental Example 1.

TABLE 2

| | medium for feces culture |
|---|---|
| Example 2-1 | 0.1% γ-PGA and 0.5% CMOS-containing PBS solution |
| Example 2-2 | 0.5% γ-PGA and 0.5% CMOS-containing PBS solution |
| Example 2-3 | 1.0% γ-PGA and 0.5% CMOS-containing PBS solution |
| Comparative Example 3 | 0.5% CMOS-containing PBS solution (positive control) |
| Reference Example 2 | PBS alone (negative control) |
| Example 3-1 | 0.1% γ-PGA and 0.5% IMOS-containing PBS solution |
| Example 3-2 | 0.5% γ-PGA and 0.5% IMOS-containing PBS solution |
| Example 3-3 | 1.0% γ-PGA and 0.5% IMOS-containing PBS solution |
| Comparative Example 4 | 0.5% IMOS-containing PBS solution (positive control) |
| Reference Example 3 | PBS alone (negative control) |
| Example 4-1 | 0.1% γ-PGA and 0.5% GOS-containing PBS solution |
| Example 4-2 | 0.5% γ-PGA and 0.5% GOS-containing PBS solution |
| Example 4-3 | 1.0% γ-PGA and 0.5% GOS-containing PBS solution |
| Comparative Example 5 | 0.5% GOS-containing PBS solution (positive control) |
| Reference Example 4 | PBS alone (negative control) |

Using the results obtained by quantitative PCR, the relative amount when PBS alone (negative control) is 1 was calculated, and the results were normalized with z-score.

Figure 2:
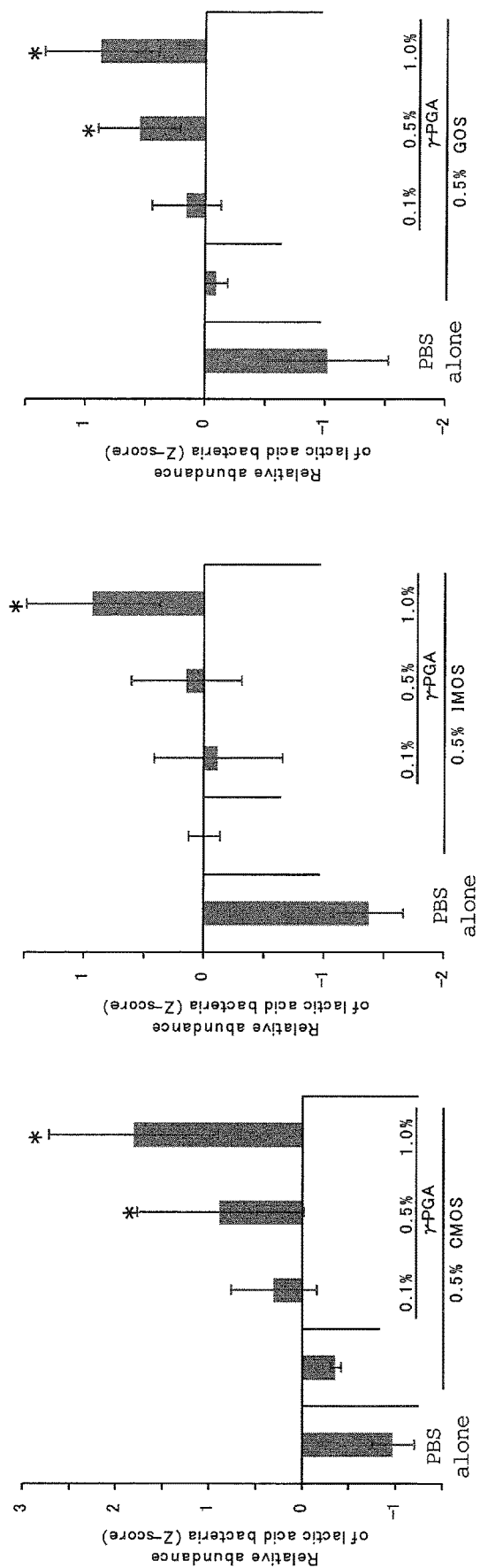
FIG. 2 shows the results (mean±standard error, n=3) of Experimental Example 2, which shows a test of the addition of γ-polyglutamic acid and various oligosaccharides to a human feces suspension.

The results are shown in FIG. 2. The data shows mean of z-score±standard error (n=3). A significant difference was determined by Dunnet's test using positive control as the control (*: P<0.05).

As a result, all oligosaccharides showed remarkable proliferation of the lactic acid bacteria group by combining with γ-PGA, as compared to when an oligosaccharide was used alone.

Thus, a synergistic effect exceeding the additive effect was observed in the proliferation of lactic acid bacteria group by combining γ-PGA and oligosaccharide irrespective of the type thereof.

Experimental Example 3: Administration Test of γ-PGA and FOS to Pigs

Six 2 to 3 months-old male pigs (HI-COOP SPF pig LWD) were purchased from ZEN-NOH, divided into 2 test groups each containing 3 pigs such that the average body weight was uniform and bred for 4 weeks at 3 pigs/pen. In each test group, 400 g/head of pig MIRAI CEX (ZEN-NOH) was fed twice per day. In each test group, the test substance was administered by the dosage and method shown in Table 3. Polyglutamic acid "CALTAKE" manufactured by Ajinomoto Co., Inc. was used as γ-PGA, and fructo-oligosaccharide "Mayoligo P granule" manufactured by Meiji Food Materia Co., Ltd. was used as FOS. After 4 weeks from the start of administration, the cecum was collected, and lactic acid bacteria in the cecal contents was examined by quantitative PCR in the same manner as in Experimental Examples 1 and 2.

TABLE 3 dose and administration method of test substance

| | |
|---|---|
| Example 5 | FOS: administration of 10 g of mixed feed for every meal<br>γ-PGA: oral administration of two cellulose capsules after every meal, each encapsulating 3 g |
| Comparative Example 6 | FOS: administration of 10 g of mixed feed for every meal<br>placebo: oral administration of two empty cellulose capsules after every meal |

Figure 3:
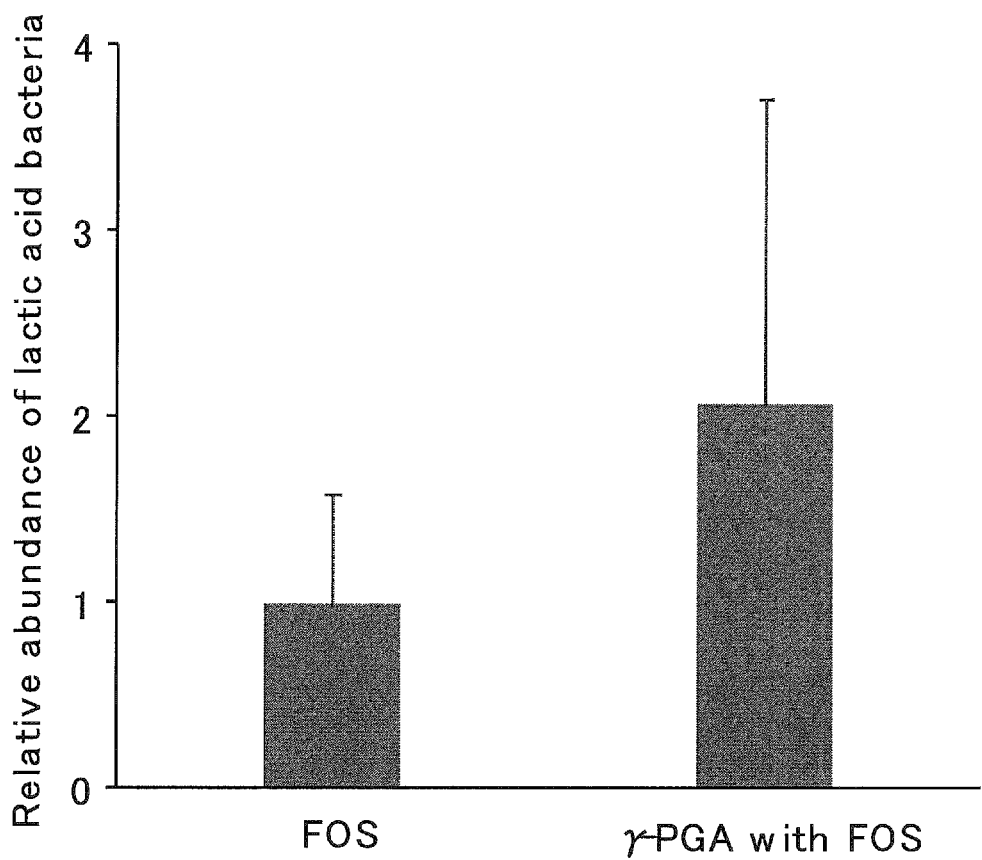
FIG. 3 shows the results (mean±standard deviation, n=3) of Experimental Example 3, which shows the results of the administration of γ-polyglutamic acid and fructo-oligosaccharide to swine.

The results are shown in FIG. 3. The data shows the relative amount when the copy number of DNA derived from lactic acid bacteria of Comparative Example 6 is 1 (mean±standard deviation, n=3).

As a result, an effect of proliferating pig intestinal lactic acid bacteria by about 2 times on average than by the ingestion of FOS alone could be confirmed by the combination of γ-PGA and FOS.

Experimental Example 4: Administration Test of γ-PGA and FOS to Pigs

Twenty-four 2 to 3 months-old male pigs (HI-COOP SPF pig LWD) were purchased from ZEN-NOH, divided into 4 test groups each containing 6 pigs such that the average body weight was uniform and bred for 4 weeks at 3 pigs/pen. In each test group, 400 g/head of pig MIRAI CEX (ZEN-NOH) was fed twice per day. In each test group, the test substance was administered by the dosage and method shown in Table 4. Polyglutamic acid "CALTAKE" manufactured by Ajinomoto Co., Inc. was used as γ-PGA, and fructo-oligosaccharide "Mayoligo P granule" manufactured by Meiji Food Materia Co., Ltd. was used as FOS. After 4 weeks from the start of administration, the cecum was collected, and bifidobacteria in the cecal contents were examined by quantitative PCR. Quantitative PCR was performed under the conditions of 45 cycles of 95° C. for 30 sec and 60° C. for 60 sec after 95° C. for 10 min. Primers for quantitative PCR used for detection bifidobacteria are as follows.

```
g-Bifid-F:
                                        (SEQ ID NO: 3)
5'-CTCCTGGAAACGGGTGG-3' g-Bifid-R:
                                        (SEQ ID NO: 4)
5'-GGTGTTCTTCCCGATATCTACA-3'
```

TABLE 4 dose and administration method of test substance

| | |
|---|---|
| Example 6 | FOS: administration of 6 g of mixed feed for every meal<br>γ-PGA: oral administration of one cellulose capsule after every meal, each encapsulating 3 g |
| Example 7 | FOS: administration of 6 g of mixed feed for every meal<br>γ-PGA: oral administration of one cellulose capsule after every meal, each encapsulating 6 g |
| Comparative Example 7 | placebo: oral administration of two empty cellulose capsules after every meal |
| Comparative Example 8 | FOS: administration of 6 g of mixed feed for every meal<br>placebo: oral administration of two empty cellulose capsules after every meal |

Figure 4:
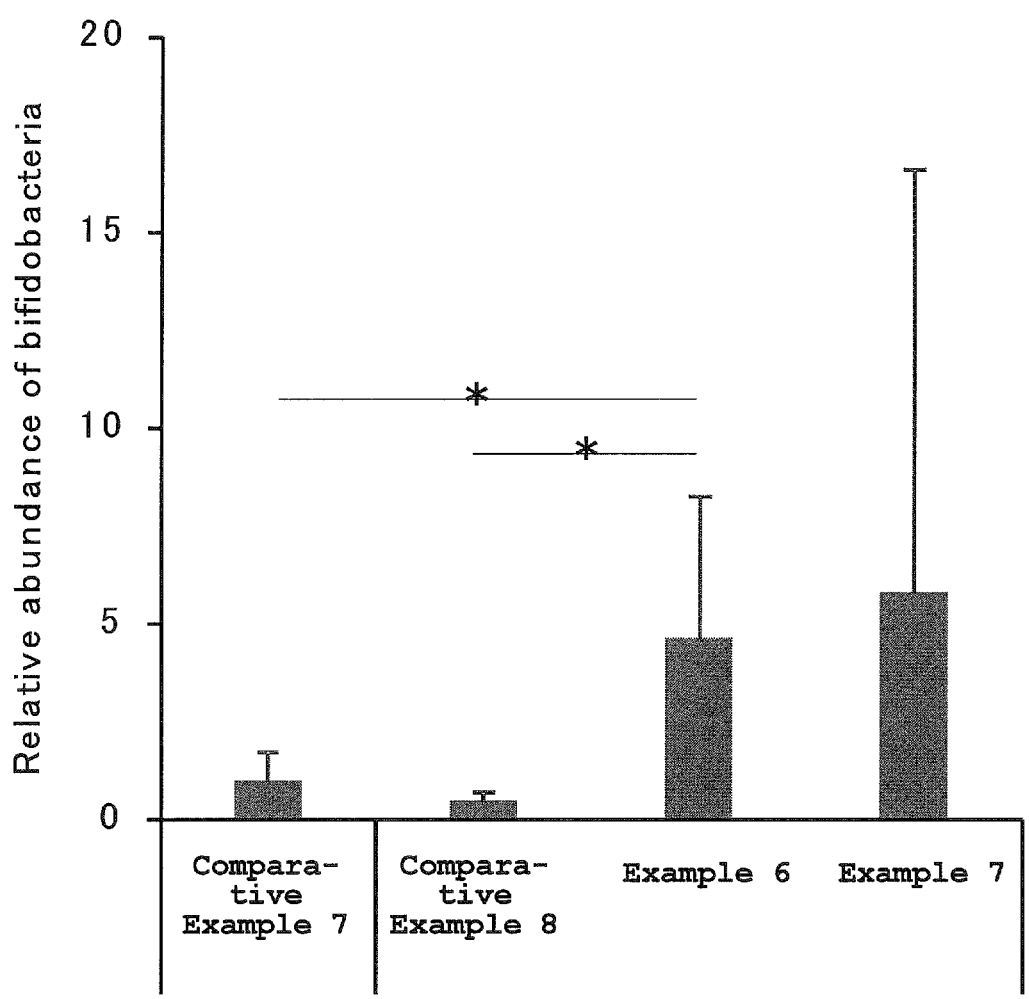
FIG. 4 shows the results (mean±standard deviation, n=6, *: P<0.05, Student's t-test) of Experimental Example 4, which shows the results of the administration of γ-polyglutamic acid and fructo-oligosaccharide to swine.

The results are shown in FIG. 4. The data shows the relative amounts when the copy number of DNA derived from bifidobacteria in Comparative Example 7 is 1 (mean±standard deviation, n=6).

As a result, an effect of proliferating pig intestinal bifidobacteria by about 10 times on average than by the ingestion of FOS alone could be confirmed by the combination of γ-PGA and FOS. In particular, a remarkable increasing effect on bifidobacteria than by the ingestion of FOS alone could be confirmed by additional ingestion of γ-PGA in half the ingestion amount of FOS.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A food for improving intestinal environment, comprising a combination of
  (1) γ-polyglutamic acid or a composition comprising γ-polyglutamic acid, and
  (2) oligosaccharide or a composition comprising oligosaccharide,
  wherein the oligosaccharide is at least one selected from the group consisting of fructo-oligosaccharide, coffee bean manno-oligosaccharide, isomalto-oligosaccharide or galacto-oligosaccharide, wherein the γ-polyglutamic acid is a polymer in which about 30 to about 5000 glutamic acids are bound, and wherein the weight ratio of the oligosaccharide and the γ-polyglutamic acid (oligosaccharide:γ-polyglutamic acid) is 1:0.1-3.

2. The food according to claim 1, wherein the composition comprising oligosaccharide is in a liquid form.

3. The food according to claim 2, wherein the composition comprising oligosaccharide in a liquid form is a liquid.

4. The food according to claim 2, wherein the composition comprising oligosaccharide in a liquid form is a drink comprising oligosaccharide.

5. The food according to claim 1, wherein the γ-polyglutamic acid is present at 0.1-20 g, per day for an adult (body weight 60 kg).

6. The food according to claim 1, wherein the oligosaccharide is present at 0.1-20 g, per day for an adult (body weight 60 kg).

7. The food of claim 1, wherein said (1) and (2) are contained in one preparation, and the preparation is in a form selected from the group consisting of powder, granule, fine granule, tablet, hard capsule, soft capsule, liquid, solution, suspension, milky liquid, liquid seasoning, liquid sweetener, drink, jelly, pudding, yogurt, candy, and chewing gum.

8. The food of claim 1, wherein said (1) and (2) are separately prepared and used in combination, wherein said (1) is a γ-polyglutamic acid or a composition containing γ-polyglutamic acid, and said (1) is in a form selected from the group consisting of powder, granule, fine granules, tablet, hard capsule, soft capsule, liquid, solution, suspension, milky liquid, drink, jelly, pudding, yogurt, candy, or chewing gum, and wherein said (2) is an oligosaccharide or a composition containing an oligosaccharide, and said (2) is in a form selected from the group consisting of powder, granule, fine granules, tablet, hard capsule, soft capsule, liquid, solution, suspension, milky liquid, liquid seasoning, liquid sweetener, drink, jelly, pudding, yogurt, candy, and chewing gum.

9. A method for improving intestinal environment, comprising administering to a subject in need thereof a combination of
  (1) γ-polyglutamic acid or a composition comprising γ-polyglutamic acid, and
  (2) oligosaccharide or a composition comprising oligosaccharide,
  wherein the oligosaccharide is at least one selected from the group consisting of fructo-oligosaccharide, coffee bean manno-oligosaccharide, isomalto-oligosaccharide or galacto-oligosaccharide, wherein the γ-polyglutamic acid is a polymer in which about 30 to about 5000 glutamic acids are bound, wherein the weight ratio of the oligosaccharide and the γ-polyglutamic acid (oligosaccharide:γ-polyglutamic acid) is 1:0.1-3.

10. The method according to claim 9, wherein the composition comprising oligosaccharide is in a liquid form.

11. The method according to claim 10, wherein the composition comprising oligosaccharide in a liquid form is a liquid.

12. The method according to claim 10, wherein the composition comprising oligosaccharide in a liquid form is a drink comprising oligosaccharide.

13. The method according to claim 9, wherein the γ-polyglutamic acid is present at 0.1-20 g, per day for an adult (body weight 60 kg).

14. The method according to claim 9, wherein the oligosaccharide is present at 0.1-20 g, per day for an adult (body weight 60 kg).

* * * * *